United States Patent [19]

Belford

[11] Patent Number: 5,725,754

[45] Date of Patent: Mar. 10, 1998

[54] METHOD OF MEASURING THE CONCENTRATION OF IONS IN SOLUTION

[76] Inventor: Rona Elizabeth Belford, 50 (2) Spylaw Road, Edinburgh EH10 5BL, United Kingdom

[21] Appl. No.: 614,736

[22] Filed: Mar. 13, 1996

[51] Int. Cl.$^6$ .................................................. G01N 27/26
[52] U.S. Cl. .................. 205/789; 205/775; 205/793; 436/150
[58] Field of Search ............................ 422/82.02, 82.03; 436/149, 150; 204/420, 418, 419; 205/775, 789, 793

[56] References Cited

U.S. PATENT DOCUMENTS

| | | | |
|---|---|---|---|
| 4,133,735 | 1/1979 | Afromowitz et al. | 204/420 |
| 4,816,118 | 3/1989 | Oyama et al. | 204/418 |
| 4,935,207 | 6/1990 | Stanbro et al. | 422/68.1 |
| 5,110,441 | 5/1992 | Kinlen et al. | 204/418 |
| 5,334,351 | 8/1994 | Heinze et al. | 422/90 |
| 5,494,831 | 2/1996 | Kindler | 422/82.03 |
| 5,567,301 | 10/1996 | Stetter et al. | 204/403 |
| 5,569,591 | 10/1996 | Kell et al. | 436/149 |

OTHER PUBLICATIONS

Gutierrez et al. Use of Complex Impedance Spectroscopy in Chemical Sensor Characterization Sensors and Actuators, 1991, pp. 359–363 No month available.

Gutierrez et al. Design of Polycrystalline Gas Sensors based on Admittance Spectrum Measurements Sensors and Actuators, 1992, pp. 609–613 No month available.

Gutierrez et al. Properties of Polycrystalline Gas Sensors Based on D.C. and A.C. Electrical Measurements, Sensors and Actuators, 1992, pp. 231–235 No month available.

*Primary Examiner*—Bruce F. Bell
*Attorney, Agent, or Firm*—Howson and Howson

[57] ABSTRACT

A method of measuring the concentration of ions in a solution, for example the concentration of solvated $H^+$ ions i.e. the pH, comprises applying an a. c. signal across an ion-sensitive material immersed in the solution and measuring the complex impedance of the ion-sensitive material at a frequency at which the out-of-phase component of the impedance is sensitive to changes in pH. A probe for use in the method comprises two metal electrodes encased in pH sensitive glass, or two electrodes coated independently with ion-sensitive glass, then fritted together.

8 Claims, 3 Drawing Sheets

METHOD OF MEASURING THE CONCENTRATION OF IONS IN SOLUTION

FIELD OF THE INVENTION

This invention relates to a method of measuring the concentration of ions in a solution. More particularly, but not exclusively, it relates to a method of measuring the pH of a solution, ie, the concentration of solvated hydrogen ions ($H^+$) in solution.

BACKGROUND TO THE INVENTION

The pH electrodes presently available are usually made from one of a variety of silicate based glasses specially developed for the purpose [4]. Many materials are also known which are selective and sensitive to other ions in solutions and electrodes containing an ion selective permeable or semi-permeable membrane are therefore available for a wide range of ions such as $Li^+$, $Na^+$, $K^+$, $Ag^+$, $Ca^{2+}$, $NH_4^+$, etc. [4, 5, 6]. In all cases these devices operate potentiometrically. A concentration dependent potential is developed across the ion selective material/solution interface which is measured against a suitable reference electrode.

Conventional ion selective electrodes are fragile high impedance structures. Solid state sensors have therefore been proposed, since these offer a low impedance, robustness and generally small size, compatible with computer controlled systems.

For example, thick-film electrodes [2, 16, 17] have tried to utilise the effect of the ion-absorption on the surface of the selective material, as a means of quantitative evaluation of the ion concentration. Other sensors, such as ion-selective-field-effect-transistors (ISFETs) have also been made; here the accumulated electrostatic charge is used to vary a dependent current [8]. This latter use of the absorbed species is instructive in that the device can only work if the sensing mechanism involves site binding.

The main obstacle to the successful production of solid state sensors is incompatibilities in their physical manufacture. Robust, long-life, fissure free, well matched and compatible solid state electrodes have not yet been produced. The basic incompatibility in forming good seals between the intrinsic materials required to fabricate these electrodes is the fundamental problem. This is apparent in the interfaces of metals, glasses and the inert substrates of thick-film devices and in the encapsulation problems of the ISFET. ISFET devices are used but as disposable sensors only. These incompatibilities may not be surmountable. The electrode response suffers markedly when additives are used to enhance strong metallurgical bonds.

DC drifts and offset-potential drifts are also disadvantages of solid state potentiometric sensors. Daily drifts arise from ionic transport due to concentration gradient electric fields imposed throughout the electrodes. Inconsistencies also arise from ineffective reference electrodes.

SUMMARY OF THE INVENTION

It is an object of the invention to provide a method of measuring ion concentrations which alleviates the above disadvantages.

Accordingly, from one aspect, the invention consists in a method of measuring the concentration of ions in a solution, comprising applying an a.c. signal across an ion-sensitive material immersed in the solution and measuring at least one of the real or imaginary components of the impedance of the ion-sensitive material.

Preferably, the a.c. signal is applied at a particular frequency which is sensitive to change in the out-of phase component of impedance when the ion-concentration is altered. For any given ion-sensitive material several such frequencies exist.

From another aspect, the invention consists in a solid probe for use in the method as described above, the probe comprising two conductive electrodes encased in a solid state ion-sensitive material between which electrodes the a.c. signal can be applied.

The electrodes may be encased in a single bead of ion-sensitive material. Alternatively, the electrodes may be separately covered with ion-sensitive material and then sintered together. Ion-sensitive materials are usually glasses, for example the pH sensitive probe may comprise soda-lime silicate glass.

The invention entails the use of a sensor for the solution phase which offers substantial advantages over the potentiometric type. While the pH sensor is used as an example, the considerations set out in the following apply equally to any other ion with appropriate choice of ion selective material.

The term "a.c. impedance" spectra has become recognized as a description of a technique which involves applying an a. c. signal to a sample or a system and plotting the real versus the imaginary parts of its response, in the complex plane, with frequency as a parameter. The data can be represented in a number of forms, as complex impedance, complex conductivity (admittance) or complex permittivity. These representations can be given for the same set of data. They can be used diagnostically, in combination with frequency and temperature data to investigate electrical processes occurring in various regions of a material.

The theory of a. c. impedance spectra is well established and a comprehensive treatment in the context of ion selective electrodes is given in a book by Buck [1]. In the inventor's previous work [2, 3] a c impedance techniques were used as diagnostic tools for investigating processes occurring at glass/metal interfaces, in the bulk glass and also relaxations due to the conduction processes occurring in the surface gel layer. The gel layer is known to be the sensitive region in ion selective glasses since it contains the active sites necessary for sensing ions in solution.

Electrochemical reactions involving the transfer of charge within a material at an electrode/solution interface or at a solid/metal interface, are composed of reaction steps which are a combination of mass transfer and activated processes. The time dependent rates of the individual steps which contribute the conduction, can be deduced by applying an electrical perturbation and monitoring the response under a variety of conditions. Transient techniques of this kind can be divided into two main categories: those using a step function or ramp stimulus and those using a small sinusoidal signal. The nature of pH sensitive glass and its interfaces is best approached via the latter, ie the a. c. impedance technique, since it provides a more direct means of determining the conduction process occurring at, for example the surface gel layer by measuring rate constants of that particular region's contribution to conduction. In the impedance spectra of soda-lime silicate glass there are generally two main relaxations; the bulk relaxation and a low frequency relaxation due to electrode polarization phenomena [7]. In the inventor's previous work [2, 3] a third major relaxation was observed and attributed to the dielectric relaxation within the hydration layer formed on the surface of the pH glass layer i.e. the gel layer. As mentioned earlier this surface is the site required for hydrogen ion sensing [4, 8, 9].

In previous work by the inventor [2, 3], a. c. impedance analysis was used to examine various electrical contacts on pH sensitive glasses. Different physical structures were examined. The two salient types were: (a) disc samples incorporating a gel layer and (b) fused samples omitting the gel layer.

Generally a combination of admittance, impedance and permittivity representations can give either directly or by extrapolation a number of physically important parameters. The DC resistance, R (and its conductance G) is obtained by extrapolating the arc to its intersection of the real impedance (Z') axis at the low frequency end of the bulk relaxation. The activation energy for d.c. conduction may be obtained by measuring spectra at different temperatures and plotting log R (or log G) versus (1/T). The bulk relaxation time $Y_\beta$ may be obtained directly from impedance spectra or from the corresponding dielectric representation. Using plots of log $Y_\beta$ versus (1/T), the bulk activation energy ($E_{act}$) $_b$ may be derived. The bulk relaxation also provides a good reference for comparing bulk properties of samples with different electrical contacts. At the loss maximum, the angular frequency, omega=$2\pi f$=$(1/Y)$, and the inverse relaxation time (1/Y) gives the rate constant k, for that conduction mechanism. The lower frequency relaxations can be due to processes occurring at the surface or at the glass/metal interface. The rates and activation energies for these processes can indicate the nature of chemical reactions or the charge transfer process at various interfaces (surfaces and metal contact interfaces) of the sample. The Arrhenius plots give not only $E_{act}$ but by extrapolating to (1/T) the pre-exponential factor "A" can be obtained. This factor is characteristic of types of activated complex, involved in the charge transfer process.

Admittance spectra recorded at room temperatures of both types of sample, (a) and (b), differed in that samples containing the gel layer exhibited an extra relaxation and further investigation at elevated activation energies for conduction ($E_{act}$) of this surface layer. Other useful parameters were obtained and are tabulated below. Slight variations (±5%) were obtained from different samples, thus average values are quoted.

TABLE 1

Physical Parameters Obtained From
AC Impedance Measurement of pH Glass Samples
At A Variety of Temperatures

| PARAMETER | BULK | GEL LAYER |
| --- | --- | --- |
| $E_{act}$ conduction | 0.76 eV | 1.00 eV |
| A factor (s#) | $9 \times 10^{13}$ | $1.4 \times 10^{14}$ |
| Resistance ($\Omega$) | $3.5 \times 10^{14}$ | $6 \times 10^4$ |
| Capacitance (F) | $4.2 \times 10^{-10}$ | $8 \times 10^{-8}$ |

As can be seen from the table the resistance of the bulk and gel layers are similar and as the bulk is very much thicker ($10^3$ times thicker) the resistivity of the gel layer is therefore far greater. These values are comparable to those obtained elsewhere [7, 10, 11]. Consistent also is the "A" factor being similar for both bulk and surface gel layers indicating that the gel relaxation is due to a transport phenomenon, ie conduction. The $E_{act}$ for conduction is also, as expected, higher in the gel layer. This relaxation may be due to hydrogen ions being responsible for carrying the charge as opposed to $Na^+$ ions.

As described above, solution and solid state a. c. impedance techniques have been used to study processes occurring within the ion selective material and at electrode interfaces. Significantly however, a. c. impedance techniques have also been used to study conductimetric gas phase sensors [12, 13, 14]. Conductimetric sensors rely on the conductivity of a selective material changing when it is subjected to a specific species. In some gas detectors various areas of material are morphologically of different structure and therefore have different responses to an electrical stimulus. They give rise to different relaxation times and their a. c. spectra can be ideally represented as shown in FIG. 1. Changes in conductivity are attributed to absorption of gas at the grain boundaries and the band structure of the sensor material bending at the surface [15] which has selectively absorbed a gas. Consequently the surface or grain boundary conductance is influenced by the atmospheric composition.

BRIEF DESCRIPTION OF THE DRAWINGS

The invention will now be described by way of example with reference to the accompanying drawings, in which.

DETAILED DESCRIPTION OF THE PREFERRED EMBODIMENTS

Figure 1:
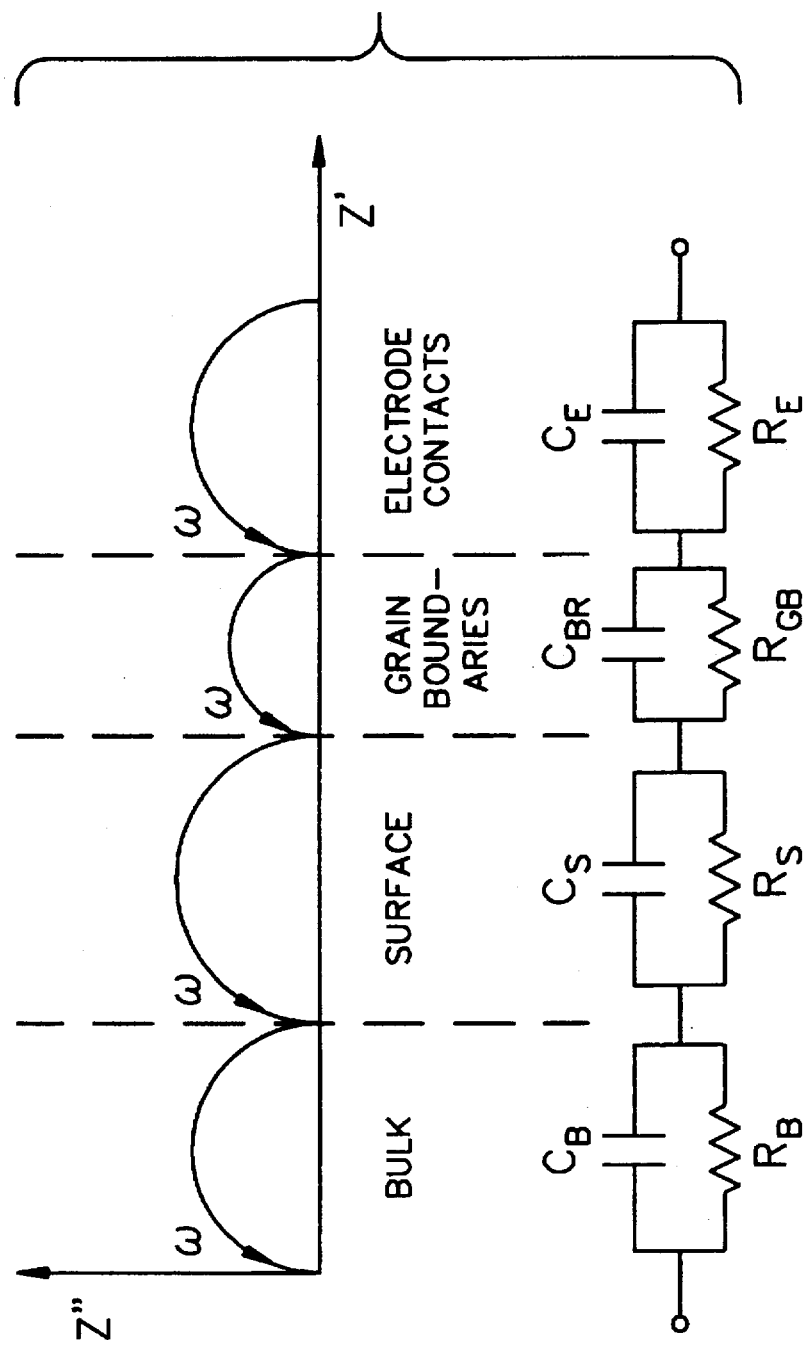
FIG. 1 shows complex impedance plots and equivalent circuits for different regions of a known conductimetric gas sensor.
Figure 2:
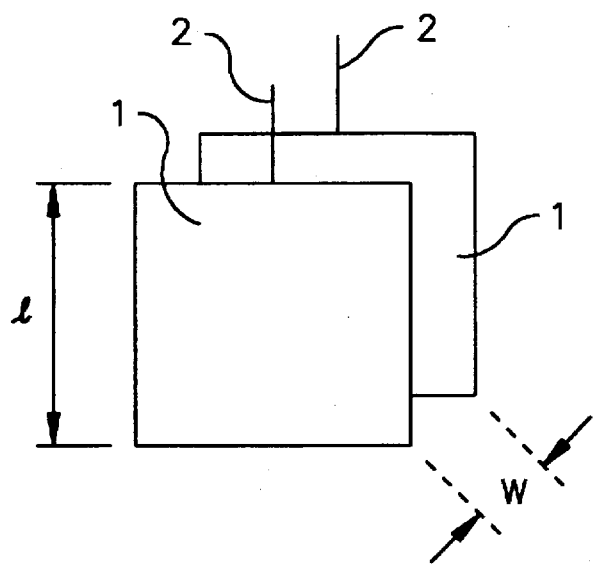
FIG. 2 is a perspective view of electrodes for use in a probe according to the invention.

FIG. 2 shows two parallel planar electrodes 1 made of conductive material, for example a suitable metal. In this example each electrode 1 comprises a square having sides of length l, and the electrodes are spaced apart by a distance W. The ratio of the area $l^2$ of the electrodes to the distance W is maximised in order to minimize the total impedance of the probe and enable accurate readings. A lead 2 is connected to each electrode 1.

Figure 3:
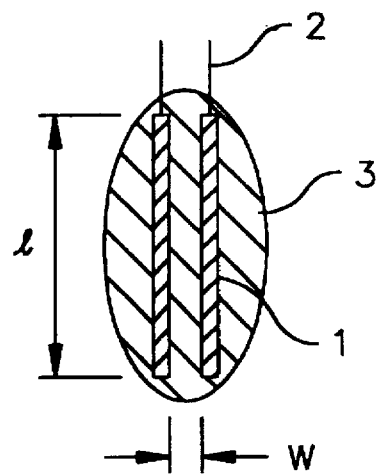
FIG. 3 is a sectional view of one embodiment of a probe incorporating the electrodes shown in FIG. 2.

FIG. 3 shows a probe which has been made by encasing the electrode 1 within a bead 3 of ion-sensitive glass, for example pH sensitive glass such as Corning 015. The leads 2 are connected to an a.c. signal generator for supplying the desired signal and also to an analyser for measuring the impedance of the system.

Figure 4:
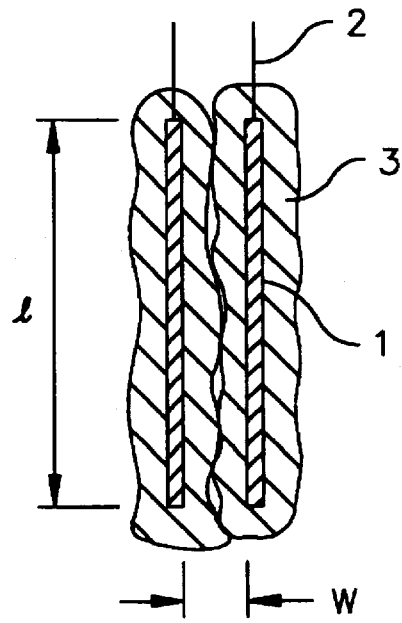
FIG. 4 is a sectional view of another embodiment of a probe incorporating the electrodes shown in FIG. 2.

An alternative embodiment of the probe is shown in FIG. 4. To make this probe, the electrodes 1 are firstly separately covered in the ion-selective material 3 (e.g. pH glass) and are then fritted or sintered together.

In the case of these pH glass probes and related selective materials, reversible absorption of the hydrated hydrogen ion changes the surface or gel layer. Complex conductivity and therefore the complex impedance of the layer changes. A. C. spectra of pH sensitive glass [2, 3] has shown a relaxation which at room temperature has a time constant, Y, in the region of one second, although variations do exist depending on the selective material used. Subjection of the glass to solutions of various pH will alter the imaginary (susceptance) and possibly the real contributions to conduction in a proportional manner.

Having isolated the appropriate room temperature single relaxation frequency, variation of the complex impedance or admittance points can be monitored as the glass is subjected to solutions of different pH strengths. Relaxation frequency values may also provide additional information.

Figure 5:
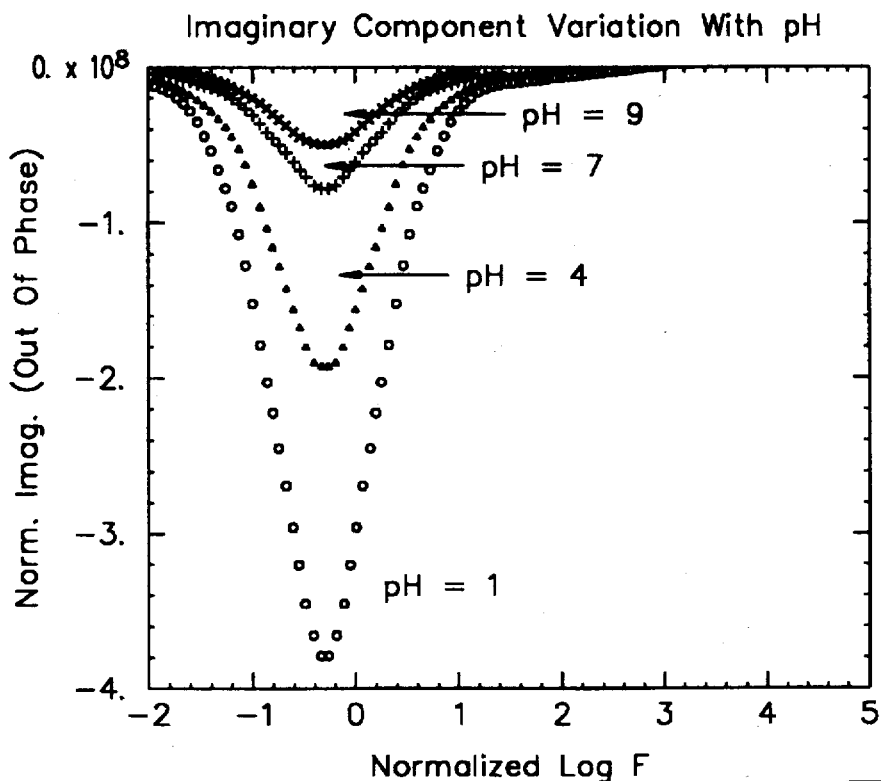
FIG. 5 is a graph of the out-of-phase component of impedance against frequency for solutions of different pH measured according to the invention.

The complex impedance spectra of such probes contain three distinct relaxations, all three of which exhibit, to a greater or lesser extent, pH sensitivity. One of these relaxations, that which occurs at the highest frequency value, is chosen here to exemplify the method. It is not the most sensitive with respect of pH, but it is the most distinct relaxation and therefore the easiest to illustrate. In a particular pH probe, as shown in FIG. 2, the highest frequency relaxation, at room temperature occurs at approximately 6.3 kHz. In an example, this relaxation was monitored as the probe was immersed into buffered solutions of various pH values. Several impedance/admittance parameters of the probe alter when it is placed in solutions of differing pH values. For example, the real or 'in-phase' component of impedance shifts with decreasing pH. The characteristic frequency of the relaxation is also shifted. The most notable change is observed in the 'imaginary' or 'out of phase' component of impedance as shown in FIG. 5. This parameter is easier and cheaper to measure than is the change of frequency with pH.

Figure 6:
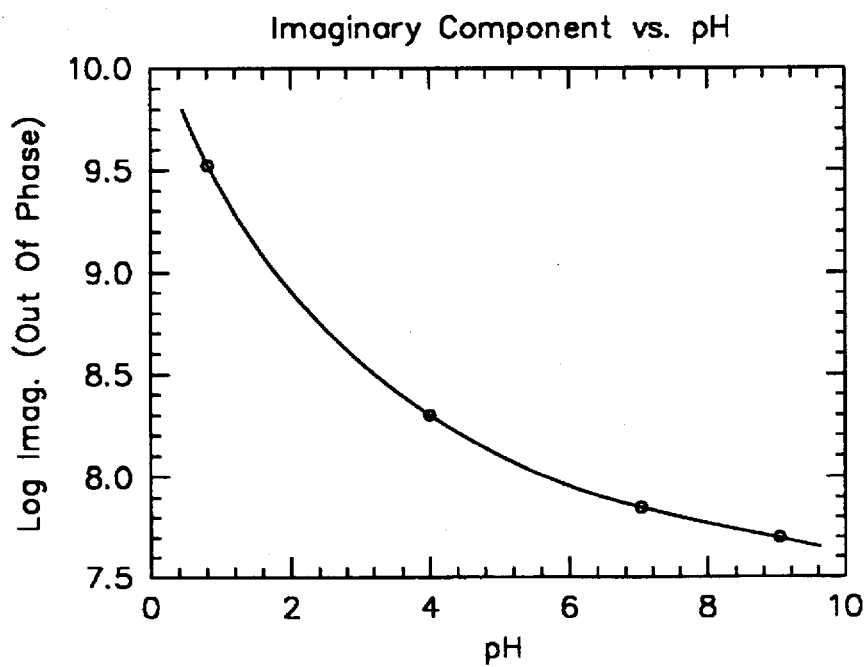
FIG. 6 is a graph of the out-of-phase component of impedance against pH for the solutions of different pH.

FIG. 5 shows how the out of phase component of impedance varies with frequency, when the sample probe is immersed in solutions of varying pH. The axes have been normalized to make their interpretation more simple. An appropriate frequency is chosen and the probe monitored in solutions of various pH. The results are also shown in FIG. 6, in terms of Log of the out of phase component measured at a single frequency, with pH as a variable parameter. As can be seen from FIG. 6, the relationship is non linear. This is true for all but a few special cases where the chosen frequency approaches, but does not reach the characteristic minimum. Here the gradients of the curves shown in FIG. 5 are very similar and a linear relation applies. The general case is that a characteristic curve is produced, the shape of which depends on the monitoring frequency chosen. Since it is repeatable and shows no hysteresis, it is a reliable measure of pH. It is also accurate and sensitive when investigated and compared to conventional methods of pH determination.

Several frequencies can be chosen for monitoring and the criteria in choosing an appropriate one must be based on both (a) the resulting sensitivity required and (b) the cost of producing a frequency generator in the region chosen.

The above method describes not only an example of a particular probe's pH response, but it also describes the parameters and processes required to produce these conductimetric ion-selective solid state sensors. The same method of measurement applies to a wide range of solid state ion-selective materials. Elevated temperatures may be required for the operation of some devices.

The a. c. measurements of the invention offers freedom from imperfections within the material structure, as the measurement does not involve a potentiometric closed circuit. Instead the sensitive surface relaxation frequency is specifically targeted and changes in conductivity monitored.

Since the present system is conductimetric a reference electrode is not required. Drift is eliminated as it is apparent only in d.c of very low frequency measurements.

The invention is applicable to many ion-selective materials, eg, ion-selective materials for the detection of $Li^+$, $Na^+$, $K^+$, $Ag^+$, $Ca^{2+}$, $Hg^{2+}$, $Pb^{2+}$ $NH_4^+$, etc [4, 5, 6].

It may be possible with a single ion-selective material, to "tune" the applied frequency to the response of more than one ion.

Modifications may be made from the specific embodiments of the invention which have been described above. The probe geometry and orientation may be varied and the electrodes may be any shape, for example, circular, grid or irregular. Any suitable pH-sensitive or other ion-selective glass may be used.

REFERENCES

1. R P Buck, "The Impedance Method Applied to the Investigation of Ion-Selective Electrodes" Ion-Selective Electrode Reviews, Vol 4 pp 3–74, (1982).
2. R E Belford, PhD Thesis, "Principles and Practice of Hybrid pH Sensors", University of Edinburgh, (1985).
3. R E Belford and A E Owen, "Temperature Dependent AC Impedance Studies of Glass to Metal contacts in Solid State Glass pH Sensors", J Non-Cyst Sol, Vol 92, No 1 pp 73–88 (1987).
4. G Eisenmann (Editor), "Glass Electrodes for Hydrogen and Other Cations", Mercel Dekker, New York, (1967).
5. J Koryta, "Ion-Selective Electrodes", Cambridge University Press, (1975).
6. H Frieser (Editor), "Ion-Selective Electrodes in Analytical Chemistry", Vol 2, Plenum Press, New York, (1980).
7. M Tomozawa "Treatise on Materials Science and Technology", Vol 12, Glass 1; Interaction with Electromagnetic Radiation, Academic Press, pp 283–343 (1977).
8. L J Bousse, "The Chemical Sensitivity of Electrolyte/Insulator/Silicon Structures—Fundamentals of The ISFET Operation", Doctorate These, Technicshe Hageskool Twente, The Netherlands, (1982).
9. T Kanazawa et al, "Characterisation of Surface OH Groups on Porous Glass", J Ceram Soc Jpn, Vol 92 (11) pp 594–654 (1984).
10. A K Jonscher, "Analysis of the Alternating Current Properties of Ionic Conductors", J Mat Sci Vol 13 pp 553–562 (1978).
11. A Wikby, "The Resistance of the Surface Layers of Glass Electrodes", Phys Chem Glasses, Vol 15 pp 37–41 (1974).
12. F J Gutierrex, L Ares, M C Horrillo, I Sayago, J Agapito and L Lopez, "Use of Complex Impedance Spectroscopy in Chemical Sensor Characterization", Sensors and Actuators B, Vol 4 pp 359–363 (1991).
13. F J Gutierrex, L Ares, J I Robla, M C Horrillo, I Sayago and J Agapito "Design of Polycrystalline Gas Senors Based on Admittance Spectrum Measurements", Sensors and Actuators B, Vol 7 pp 609–613 (1992).
14. F J Gutierrex, L Ares, J I Robla, M C Horrillo, I Sayago and J Agapito "Properties of Polycrystalline Gas Sensors Based on DC and AC Electrical Measurements", Sensors and Actuators B, Vol 8 pp 231–235 (1992).
15. G Hiland, "Homogeneous Semiconducting Gas Sensors", Sensors and Actuators, Vol 2 pp 343–361 (1982).
16. R E Belford, R G Kelly and A E Owen, "Thick Film Devices", Invited Chapter in "Chemical Sensors" T E Edmond (Editor) Blackie & Son Ch 11 pp 236–255 (1988).
17. R E Belford, A E Owen and R G Kelly, "Thick-Film Hybrid pH Sensors", Sensors and Actuators 11 pp 387–398 (1987).

I claim:

1. A method of measuring the concentration of ions in a solution, comprising applying an a.c. signal across an ion-sensitive material immersed in the solution and measuring one of the real and imaginary components of the impedance of the ion-sensitive material separately from the other of said components.

2. The method of claim 1, comprising measuring the imaginary component of the impedance of the ion-sensitive material separately from the real component.

3. The method of claim 2, wherein the a.c. signal is applied at a particular frequency at which the imaginary component of impedance is more sensitive to alterations in the ion concentration than at other frequencies.

4. The method of claim 2, wherein the a.c. signal is applied at a particular frequency at which the sensitivity of the imaginary component of impedance to alterations in the ion concentration is substantially at a peak.

5. The method of claim 1 in which the a.c. signal is applied to two conductive electrodes encased in a solid state ion-sensitive material.

6. The method of claim 5 wherein the electrodes are encased in a single bead of ion-sensitive material.

7. The method of claim 6 wherein the electrodes are separately covered in ion-sensitive material and then sintered together.

8. The method of claim 6, wherein the ion-sensitive material comprises ion-sensitive glass.

* * * * *